US008783258B2

(12) United States Patent
Jacobs et al.

(10) Patent No.: US 8,783,258 B2
(45) Date of Patent: Jul. 22, 2014

(54) IMPLANT SYSTEMS AND METHODS FOR TREATING OBSTRUCTIVE SLEEP APNEA

(75) Inventors: John Jacobs, Easton, PA (US); Kevin S. Weadock, Hillsborough, NJ (US); Robert A. Rousseau, Ottsville, PA (US); David Lindh, Sr., Flemington, NJ (US)

(73) Assignee: Ethicon, Inc., Somerville, NJ (US)

( * ) Notice: Subject to any disclaimer, the term of this patent is extended or adjusted under 35 U.S.C. 154(b) by 579 days.

(21) Appl. No.: 12/325,350

(22) Filed: Dec. 1, 2008

(65) Prior Publication Data

US 2010/0132719 A1    Jun. 3, 2010

(51) Int. Cl.
| A61F 5/37 | (2006.01) |
| A61F 13/00 | (2006.01) |
| A61C 5/14 | (2006.01) |
| A61B 19/00 | (2006.01) |
| A61B 17/56 | (2006.01) |
| A61F 5/04 | (2006.01) |
| A61B 17/58 | (2006.01) |
| A61F 2/30 | (2006.01) |
| A61B 17/70 | (2006.01) |
| A61F 2/20 | (2006.01) |
| A61F 2/02 | (2006.01) |
| A61F 2/08 | (2006.01) |

(52) U.S. Cl.
USPC ........... 128/848; 128/846; 128/860; 128/897; 128/898; 128/899; 602/902; 606/53; 606/60; 606/251; 606/263; 623/9; 623/11.11; 623/14.13; 623/17.17

(58) Field of Classification Search
CPC .............. A61F 2/00; A61F 2/02; A61F 2/08; A61F 2/0805; A61F 2/0811; A61F 5/56; A61F 5/566; A61B 17/1671; A61B 17/663; A61B 17/7032; A61B 17/7052

USPC ............. 128/846, 848, 897–899, 860; 623/9, 623/11.11, 14.13, 17.17; 602/902; 606/53, 606/60, 251, 263
See application file for complete search history.

(56) References Cited

U.S. PATENT DOCUMENTS

| 3,123,077 A | 3/1964 | Alcamo |
| 3,378,010 A | 4/1968 | Codling et al. |

(Continued)

FOREIGN PATENT DOCUMENTS

| CN | 2465680 | 12/2001 |
| CN | 201029957 Y | 3/2008 |

(Continued)

OTHER PUBLICATIONS

Shamsuzzman, et al., "Obstructive Sleep Apnea; Implications for Cardiac and Vascular Disease", JAMA, vol. 290: (14); pp. 1906-1914.

(Continued)

Primary Examiner — Patricia Bianco
Assistant Examiner — Brandon L Jackson

(57) ABSTRACT

A system for treating obstructive sleep apnea includes an anchoring element having scar tissue located in an inframandibular region, and a tongue implant having at least one arm extending therefrom, whereby the tongue implant is implantable in a tongue with the at least one arm being connectable with the anchoring element for coupling the tongue implant with the anchoring element. In one embodiment, the anchoring element includes a first implant part such as a flexible layer implantable in the inframandibular region and the scar tissue is formed on, in, and/or around the first implant part. The tongue implant is coupled with the anchoring element and/or the scar tissue through the at least one arm. The length of the at least one arm may be adjusted for shifting the tongue anteriorly.

19 Claims, 9 Drawing Sheets

(56) References Cited

U.S. PATENT DOCUMENTS

| | | |
|---|---|---|
| 4,069,825 A | 1/1978 | Akiyama |
| 4,290,763 A | 9/1981 | Hurst |
| 4,557,264 A | 12/1985 | Hinsch |
| 4,839,215 A | 6/1989 | Starling et al. |
| 4,881,939 A | 11/1989 | Newman |
| 4,950,285 A | 8/1990 | Wilk |
| 5,053,047 A | 10/1991 | Yoon |
| 5,123,913 A | 6/1992 | Wilk et al. |
| 5,192,271 A | 3/1993 | Kalb et al. |
| 5,192,274 A | 3/1993 | Bierman |
| 5,269,783 A | 12/1993 | Sander |
| 5,284,161 A | 2/1994 | Karell |
| 5,311,028 A | 5/1994 | Glavish |
| 5,393,984 A | 2/1995 | Glavish |
| 5,483,077 A | 1/1996 | Glavish |
| 5,484,444 A | 1/1996 | Braunschweiler et al. |
| 5,609,559 A | 3/1997 | Weitzner |
| 5,683,417 A | 11/1997 | Cooper |
| 5,704,895 A | 1/1998 | Scott et al. |
| 5,792,067 A | 8/1998 | Karell |
| 5,843,077 A | 12/1998 | Edwards |
| 5,931,855 A | 8/1999 | Buncke |
| 6,161,541 A | 12/2000 | Woodson |
| 6,190,401 B1 | 2/2001 | Green et al. |
| 6,241,747 B1 | 6/2001 | Ruff |
| 6,250,307 B1 | 6/2001 | Conrad et al. |
| 6,348,156 B1 | 2/2002 | Vishnoi et al. |
| 6,431,174 B1 | 8/2002 | Knudson et al. |
| 6,432,437 B1 | 8/2002 | Hubbard |
| 6,457,472 B1 | 10/2002 | Schwartz et al. |
| 6,513,530 B2 | 2/2003 | Knudson et al. |
| 6,523,542 B2 | 2/2003 | Knudson et al. |
| 6,578,580 B2 | 6/2003 | Conrad et al. |
| 6,589,549 B2 | 7/2003 | Shih et al. |
| 6,599,310 B2 | 7/2003 | Leung et al. |
| 6,627,600 B2 | 9/2003 | Boutignon |
| 6,634,362 B2 | 10/2003 | Conrad et al. |
| 6,638,284 B1 | 10/2003 | Rousseau et al. |
| 6,716,251 B1 | 4/2004 | Asius et al. |
| 6,742,524 B2 | 6/2004 | Knudson et al. |
| 6,755,868 B2 | 6/2004 | Rousseau |
| 6,800,082 B2 | 10/2004 | Rousseau |
| 6,899,105 B2 | 5/2005 | Krueger et al. |
| 6,955,172 B2 | 10/2005 | Nelson et al. |
| 6,981,944 B2 | 1/2006 | Jamiolkowski et al. |
| 7,017,582 B2 | 3/2006 | Metzger et al. |
| 7,056,331 B2 | 6/2006 | Kaplan et al. |
| 7,135,189 B2 | 11/2006 | Knapp |
| 7,146,981 B2 | 12/2006 | Knudson et al. |
| 7,166,570 B2 | 1/2007 | Hunter et al. |
| 7,213,599 B2 | 5/2007 | Conrad et al. |
| 7,237,554 B2 | 7/2007 | Conrad et al. |
| 7,261,702 B1 | 8/2007 | Alexandre et al. |
| 7,288,075 B2 | 10/2007 | Parihar et al. |
| 7,297,102 B2 | 11/2007 | Smith et al. |
| 7,322,993 B2 | 1/2008 | Metzger et al. |
| 7,337,781 B2 | 3/2008 | Vassallo |
| 7,360,432 B2 | 4/2008 | Lehtonen |
| 7,360,542 B2 | 4/2008 | Nelson et al. |
| 7,367,340 B2 | 5/2008 | Nelson et al. |
| 7,401,611 B2 | 7/2008 | Conrad et al. |
| 7,442,389 B2 | 10/2008 | Quelle et al. |
| 7,601,164 B2 | 10/2009 | Wu |
| 7,669,603 B2 | 3/2010 | Knudson et al. |
| 7,806,908 B2 | 10/2010 | Ruff |
| 7,850,894 B2 | 12/2010 | Lindh, Sr. et al. |
| 7,857,829 B2 | 12/2010 | Kaplan et al. |
| 7,888,119 B2 | 2/2011 | Sugaya et al. |
| 8,142,422 B2 | 3/2012 | Makower et al. |
| 8,307,831 B2 | 11/2012 | Rousseau |
| 8,413,661 B2 | 4/2013 | Rousseau et al. |
| 2001/0037133 A1 | 11/2001 | Knudson et al. |
| 2002/0144685 A1 | 10/2002 | Ivanovich et al. |
| 2003/0004579 A1 | 1/2003 | Rousseau et al. |
| 2003/0034312 A1 | 2/2003 | Unger et al. |
| 2003/0149445 A1 | 8/2003 | Knudson et al. |
| 2003/0149447 A1 | 8/2003 | Morency et al. |
| 2003/0149488 A1 | 8/2003 | Metzger et al. |
| 2003/0176875 A1 | 9/2003 | Anderson et al. |
| 2004/0020492 A1 | 2/2004 | Dubrul et al. |
| 2004/0020498 A1 | 2/2004 | Knudson et al. |
| 2004/0028676 A1 | 2/2004 | Klein et al. |
| 2004/0044366 A1 | 3/2004 | Bonutti et al. |
| 2004/0102796 A1 | 5/2004 | Hill et al. |
| 2004/0139975 A1 | 7/2004 | Nelson et al. |
| 2004/0144395 A1 | 7/2004 | Evans et al. |
| 2004/0147811 A1 | 7/2004 | Diederich et al. |
| 2004/0149290 A1 | 8/2004 | Nelson et al. |
| 2004/0153127 A1 | 8/2004 | Gordon et al. |
| 2004/0231678 A1 | 11/2004 | Fierro |
| 2005/0038472 A1 | 2/2005 | Furst |
| 2005/0092334 A1 | 5/2005 | Conrad et al. |
| 2005/0115572 A1 | 6/2005 | Brooks et al. |
| 2005/0121039 A1 | 6/2005 | Brooks et al. |
| 2005/0159637 A9 | 7/2005 | Nelson et al. |
| 2005/0165352 A1 | 7/2005 | Henry et al. |
| 2005/0199248 A1 | 9/2005 | Pflueger et al. |
| 2005/0203576 A1 | 9/2005 | Sulamanidze |
| 2005/0251255 A1 | 11/2005 | Metzger et al. |
| 2005/0267321 A1 | 12/2005 | Shadduck |
| 2005/0267531 A1 | 12/2005 | Ruff et al. |
| 2005/0267532 A1 | 12/2005 | Wu |
| 2005/0267571 A1 | 12/2005 | Spence et al. |
| 2005/0279365 A1 | 12/2005 | Armijo et al. |
| 2006/0005843 A9 | 1/2006 | Nelson et al. |
| 2006/0079935 A1 | 4/2006 | Kolster |
| 2006/0083767 A1 | 4/2006 | Deusch et al. |
| 2006/0093644 A1 | 5/2006 | Quelle et al. |
| 2006/0150986 A1 | 7/2006 | Roue et al. |
| 2006/0185673 A1 | 8/2006 | Critzer et al. |
| 2006/0206197 A1 | 9/2006 | Morsi |
| 2006/0207608 A1 | 9/2006 | Hirotsuka et al. |
| 2006/0207612 A1 | 9/2006 | Jackson et al. |
| 2006/0228391 A1 | 10/2006 | Seyedin et al. |
| 2006/0241339 A1 | 10/2006 | Cook et al. |
| 2006/0266369 A1 | 11/2006 | Atkinson et al. |
| 2006/0289015 A1 | 12/2006 | Boucher et al. |
| 2007/0000497 A1 | 1/2007 | Boucher et al. |
| 2007/0005109 A1 | 1/2007 | Popadiuk et al. |
| 2007/0005110 A1 | 1/2007 | Collier et al. |
| 2007/0102004 A1 | 5/2007 | Nelson et al. |
| 2007/0102010 A1 | 5/2007 | Lemperle et al. |
| 2007/0110788 A1 | 5/2007 | Hissong et al. |
| 2007/0119463 A1 | 5/2007 | Nelson et al. |
| 2007/0123996 A1 | 5/2007 | Sugaya et al. |
| 2007/0144531 A1 | 6/2007 | Tomas et al. |
| 2007/0144534 A1 | 6/2007 | Mery et al. |
| 2007/0144535 A1 | 6/2007 | Hegde et al. |
| 2007/0190108 A1 | 8/2007 | Datta et al. |
| 2007/0204866 A1 | 9/2007 | Conrad et al. |
| 2007/0209665 A1 | 9/2007 | Gillis et al. |
| 2007/0227545 A1 | 10/2007 | Conrad et al. |
| 2007/0233276 A1 | 10/2007 | Conrad et al. |
| 2007/0246052 A1 | 10/2007 | Hegde et al. |
| 2007/0256693 A1 | 11/2007 | Paraschac et al. |
| 2007/0257395 A1 | 11/2007 | Lindh et al. |
| 2007/0261701 A1 | 11/2007 | Sanders |
| 2007/0267027 A1 | 11/2007 | Nelson et al. |
| 2007/0270631 A1 | 11/2007 | Nelson et al. |
| 2007/0272257 A1 | 11/2007 | Nelson et al. |
| 2007/0288057 A1 | 12/2007 | Kuhnel |
| 2007/0295338 A1 | 12/2007 | Loomas et al. |
| 2007/0295340 A1 | 12/2007 | Buscemi |
| 2008/0023012 A1 | 1/2008 | Dineen et al. |
| 2008/0035158 A1 | 2/2008 | Pflueger et al. |
| 2008/0035160 A1 | 2/2008 | Woodson et al. |
| 2008/0066764 A1 | 3/2008 | Paraschac et al. |
| 2008/0066765 A1 | 3/2008 | Paraschac et al. |
| 2008/0066767 A1 | 3/2008 | Paraschac et al. |
| 2008/0066769 A1 | 3/2008 | Dineen et al. |
| 2008/0078411 A1 | 4/2008 | Buscemi et al. |
| 2008/0146868 A1 | 6/2008 | Henri Robert et al. |
| 2008/0167614 A1 | 7/2008 | Tolkowsky et al. |
| 2008/0199824 A1 | 8/2008 | Hargadon |

(56) References Cited

U.S. PATENT DOCUMENTS

| | | |
|---|---|---|
| 2008/0208265 A1 | 8/2008 | Frazier et al. |
| 2008/0221684 A1 | 9/2008 | Nelson et al. |
| 2008/0312688 A1 | 12/2008 | Nawrocki et al. |
| 2009/0025734 A1 | 1/2009 | Doelling et al. |
| 2009/0078411 A1 | 3/2009 | Kenison et al. |
| 2009/0165803 A1 | 7/2009 | Bhat et al. |
| 2010/0023055 A1 | 1/2010 | Rousseau |
| 2010/0024830 A1 | 2/2010 | Rousseau |
| 2010/0030011 A1 | 2/2010 | Weadock |
| 2010/0037901 A1 | 2/2010 | Rousseau et al. |
| 2010/0080791 A1 | 4/2010 | Rousseau et al. |
| 2010/0106246 A1 | 4/2010 | Rousseau et al. |
| 2010/0108077 A1 | 5/2010 | Lindh |
| 2010/0132719 A1 | 6/2010 | Jacobs et al. |
| 2010/0137794 A1 | 6/2010 | Knudson et al. |
| 2010/0137905 A1 | 6/2010 | Weadock et al. |
| 2010/0158854 A1 | 6/2010 | Puisais |
| 2010/0163056 A1 | 7/2010 | Tschopp et al. |
| 2010/0211184 A1 | 8/2010 | Rousseau et al. |
| 2010/0234794 A1 | 9/2010 | Weadock et al. |
| 2010/0234946 A1 | 9/2010 | Rousseau |
| 2010/0256443 A1 | 10/2010 | Griguol |
| 2010/0294284 A1 | 11/2010 | Hohenhorst et al. |
| 2010/0319710 A1 | 12/2010 | Sharkawy et al. |
| 2011/0054522 A1 | 3/2011 | Lindh, Sr. et al. |
| 2011/0100376 A1 | 5/2011 | Rousseau |
| 2011/0100377 A1 | 5/2011 | Weadock et al. |
| 2011/0100378 A1 | 5/2011 | Rousseau |
| 2011/0144558 A1 | 6/2011 | Rousseau |
| 2011/0174315 A1 | 7/2011 | Zhang et al. |
| 2011/0178439 A1 | 7/2011 | Irwin et al. |
| 2011/0238111 A1 | 9/2011 | Frank |
| 2012/0123449 A1 | 5/2012 | Schaller et al. |
| 2012/0245629 A1 | 9/2012 | Gross et al. |
| 2013/0074849 A1 | 3/2013 | Rousseau et al. |
| 2013/0098371 A1 | 4/2013 | Rousseau et al. |
| 2013/0118505 A1 | 5/2013 | Rousseau et al. |
| 2013/0133669 A1 | 5/2013 | Rousseau |
| 2013/0150872 A1 | 6/2013 | Rousseau |
| 2013/0174857 A1 | 7/2013 | Rousseau et al. |
| 2013/0186412 A1 | 7/2013 | Weadock et al. |
| 2013/0319427 A1 | 12/2013 | Sung et al. |

FOREIGN PATENT DOCUMENTS

| | | |
|---|---|---|
| CN | 102198010 | 9/2011 |
| DE | 10245076 | 4/2004 |
| EP | 2145587 | 1/2010 |
| EP | 2386252 A1 | 11/2011 |
| EP | 2517633 | 10/2012 |
| FR | 2651113 | 3/1991 |
| JP | 2001145646 | 5/2001 |
| JP | 2003265621 | 9/2003 |
| RU | 2005447 | 1/1994 |
| RU | 2202313 | 4/2003 |
| SU | 927236 | 5/1982 |
| SU | 1697792 | 12/1991 |
| WO | WO 97/13465 | 4/1997 |
| WO | 9900058 | 1/1999 |
| WO | 0066050 | 11/2000 |
| WO | 0121107 | 3/2001 |
| WO | 03096928 | 11/2003 |
| WO | WO 2004/016196 A2 | 2/2004 |
| WO | WO 2004/016196 A3 | 2/2004 |
| WO | 2004020492 | 3/2004 |
| WO | 2004021869 | 3/2004 |
| WO | 2004021870 | 3/2004 |
| WO | 2004060311 | 7/2004 |
| WO | 2004084709 | 10/2004 |
| WO | 2005046554 | 5/2005 |
| WO | 2005051292 | 6/2005 |
| WO | 2005082452 | 9/2005 |
| WO | 2005122954 | 12/2005 |
| WO | WO 2006/012188 A1 | 2/2006 |
| WO | 2006072571 | 7/2006 |
| WO | 2006108145 | 10/2006 |
| WO | WO 2007/056583 A1 | 5/2007 |
| WO | 2007075394 | 7/2007 |
| WO | 2007132449 | 11/2007 |
| WO | 2007134005 | 11/2007 |
| WO | 2007146338 | 12/2007 |
| WO | 2007149469 | 12/2007 |
| WO | 2008118913 | 10/2008 |
| WO | 2009023256 | 2/2009 |
| WO | 2009036094 | 3/2009 |
| WO | WO 2010/019376 A2 | 2/2010 |
| WO | WO 2010/019376 A3 | 2/2010 |
| WO | WO 2010/035303 A1 | 4/2010 |
| WO | 2010065341 | 6/2010 |
| WO | WO 2012/004758 | 1/2012 |
| WO | 2012041205 | 4/2012 |
| WO | 2012064902 | 5/2012 |
| WO | 2012170468 | 12/2012 |

OTHER PUBLICATIONS

Schwartz, et al., "Effects of electrical stimulation to the soft palate on snoring and obstructive sleep apnea", J. Prosthetic Denistry, pp. 273-281 (1986).

Wiltfang, et al., "First results on daytime submandibular elxtrostimulation of suprahyoidal muscles to prevent night-time hypopharyngeal collapse in obstructive sleep apnea syndrome", International Journal of Oral & Maxillofacial Surgery, pp. 21-25 (1999).

Harries, et al., "The Surgical treatment of snoring", Journal of Laryngology and Otology, pp. 1105-1106 (1996).

Huang, et al., "Biomechanics of snoring", Endeavour, vol. 19 (3): pp. 96-100 (1995).

Schwab, et al., "Upper airway and soft tissue changes induced by CPAP in normal subjects", Am. J. Respit. Crit. Care Med., vol. 154, No. 4, Oct. 1996, 1106-1116.

The Advance System, Aspire Medical, Inc., www.aspiremedical.com, 3 pp. (2008).

Pang, Kenny et al., "Tongue Suspension Suture in Obstructive Sleep Apnea," Operative Techniques in Otolaryngology, vol. 17, No. 4, Dec. 2006, pp. 252-256.

Repose Genioglossus Advancement, Influent Medical, www.influent.com, 1 page. (2008).

The Pillar Procedure, Restore Medical, Inc., www.restoremedical.com, 2 pp. (2008).

Cole, et al., "Snoring: A review and a Reassessment", Journal of Otolaryngology, pp. 303-306 (1995).

Teles et al., "Use of Palatal Lift Prosthesis on Patient Submitted to Maxillectomy: A Case Report", Applied Cancer Res. 2005, vol. 25(3), pp. 151-154.

Vicente et al., "Tongue-Base Suspension in Conjunction with Uvulopapatopharyngoplasty for Treatement of Severe Obstructive Sleep Apnea: Long-term Follow-Up Results", The Laryngoscope, vol. 115(7), pp. 1223-1227 (2006).

Wassmuth et al., "Cautery-assisted palatal stiffening operation for the treatment of obstructive sleep apnea syndrome", Otolaryngology—Head and Neck Surgery, vol. 123(1), pp. 55-60 (Jul. 2000).

Notification of Transmittal of the International Search Report and the Written Opinion of the International Search Authority or the Declaration mailed on Feb. 3, 2010; PCT/US2009/051921; International Filing Date: Jul. 28, 2009.

Notification of Transmittal of the International Search Report and the Written Opinion of the International Search Authority or the Declaration mailed on May 25, 2010; PCT/US2010/023152; International Filing Date: Apr. 2, 2010.

International Search Report dated Nov. 4, 2009 for International Patent Application No. PCT/US2009/052126.

International Search Report dated Dec. 21, 2009 for International Patent Application No. PCT/US2009/057661.

International Search Report dated Dec. 22, 2009 for International Patent Application No. PCT/US2009/061223.

International Search Report dated May 25, 2010 for International Patent Application No. PCT/US2010/025778.

(56) References Cited

OTHER PUBLICATIONS

Schleef et al., "Cytokine Activation of Vascular Endothelium, Effects on Tissue-Type 1 Plasminogen Activator Inhibitor" the J. of Biological Chem., vol. 263, No. 12, pp. 5797-5803 (1988).
International Search Report dated Jan. 14, 2011 for International Patent Application No. PCT/US2010/052628.
International Search Report dated Jan. 20, 2011 for International Patent Application No. PCT/US2010/052644.
International Search Report dated Jan. 24, 2011 for International Patent Application No. PCT/US2010/052649.
International Search Report dated Feb. 28, 2011 for International Patent Application No. PCT/US2010/059673.
International Search Report dated Jan. 21, 2010 for International Patent Application No. PCT/US2009/052110.
International Search Report dated Dec. 29, 2009 for International Patent Application No. PCT/US2009/061455.
Database: WPI Week 198312, Thomson Scientific, London, GB; AN 1983-D9513K XP 002693421.
Medtronic AIRvance System for Obstructive Sleep Apnea. http://www.medtronic.com/for-healthcare-professionals/products-therapies/ear-nose-throat/sleep-disordered-breathing-products/airvance-system-for-obstructive-sleep-apnea/index.htm.
U.S. Appl. No. 13/307,482, filed Nov. 30, 2011.
International Search Report dated Apr. 29, 2010 for International Patent Application No. PCT/US2009/065293.
U.S. Appl. No. 13/486,293, filed Jun. 1, 2012.
Database WPI Week 198312, Thomson Scientific, London, GB; AN 1983-D9513K XP002693421, -& SU 927 236 A1 (Petrozazodsk Univ) May 15, 1982 abstract (see figures 7 & 8).
International Search Report dated May 25, 2010 for International Patent Application No. PCT/US2010/023152.
International Search Report dated Apr. 9, 2013 for International Patent Application No. PCT/US2012/061569.
International Search Report dated Apr. 2, 2013 for International Patent Application No. PCT/US2012/067708.
Written Opinion dated Nov. 27, 2012 for International Patent Application No. PCT/US2012/056577.
U.S. Appl. No. 61/203,758, filed Dec. 29, 2008, p. 8 & p. 6/8.

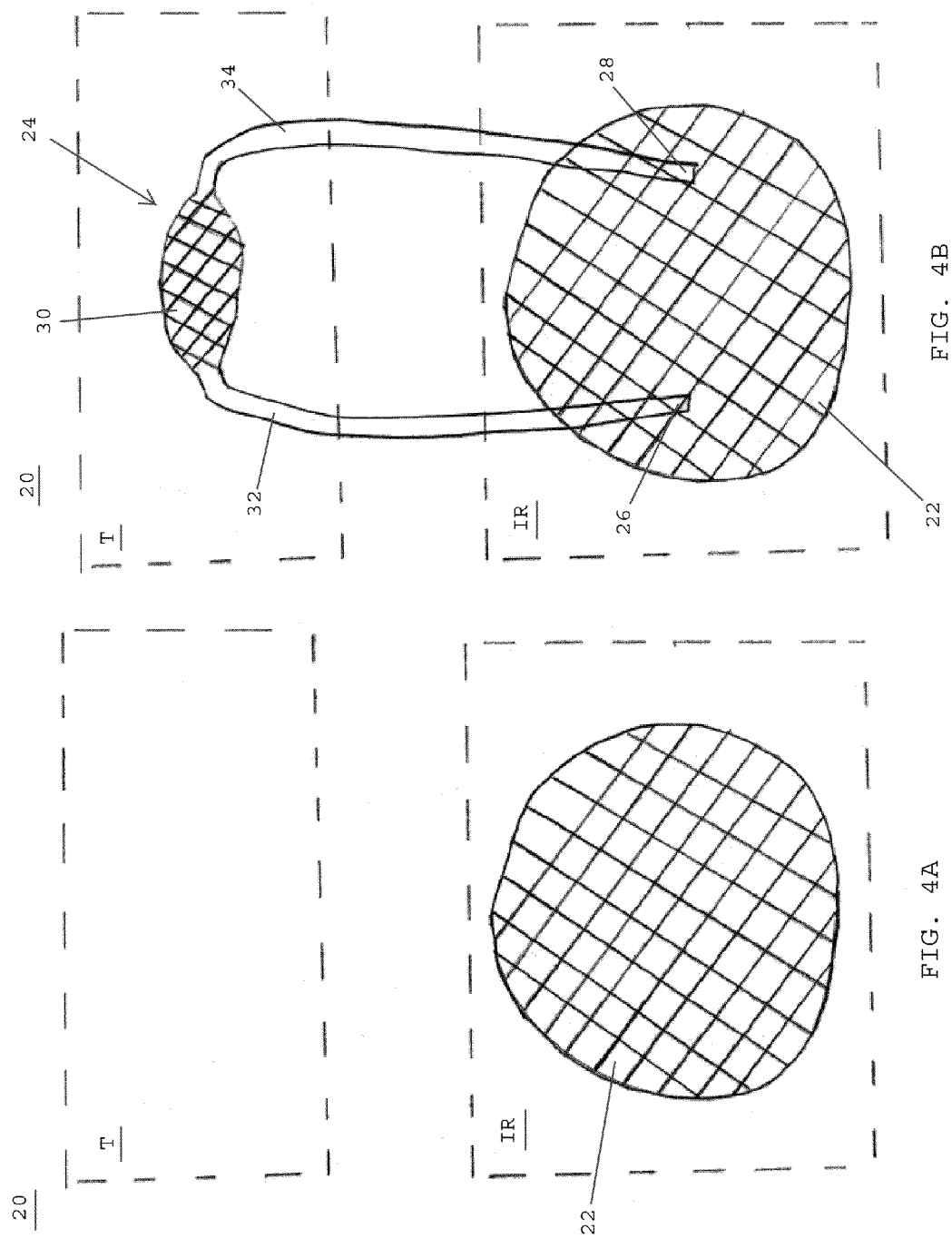

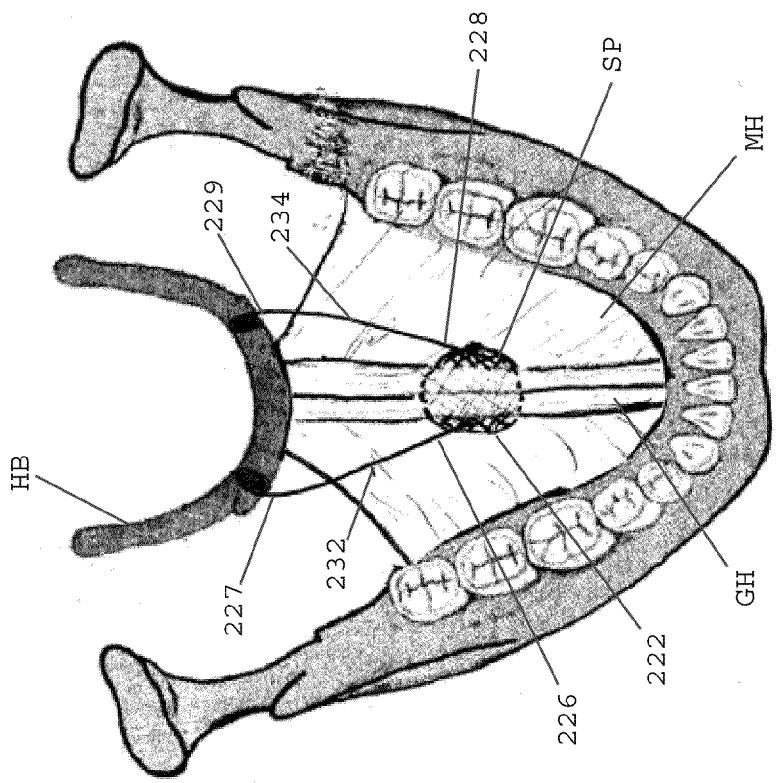
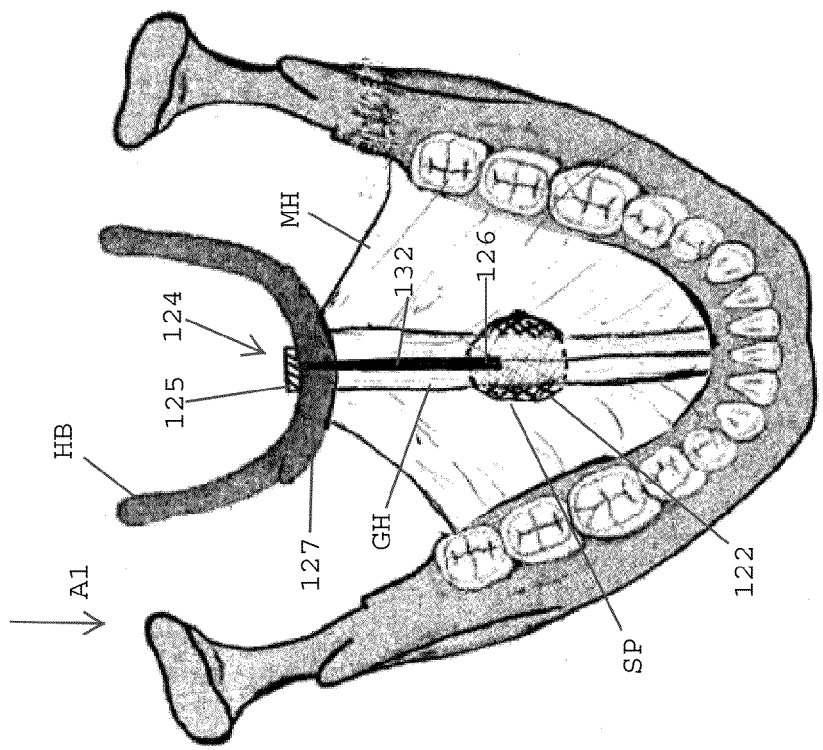
FIG. 10
FIG. 9

IMPLANT SYSTEMS AND METHODS FOR TREATING OBSTRUCTIVE SLEEP APNEA

BACKGROUND OF THE INVENTION

1. Field of the Invention

The present invention generally relates to treating sleep disorders, and more specifically relates to implant systems, devices and methods for treating patients suffering from obstructive sleep apnea.

2. Description of the Related Art

Obstructive sleep apnea (OSA) is caused by a blockage of the airway, which usually occurs when the soft tissue in the throat collapses and closes during sleep. According to the National Institutes of Health, OSA affects more than twelve million Americans. During each apnea event, the brain briefly arouses the sufferer in order to initiate the resumption of breathing. This type of sleep, however, is extremely fragmented and of poor quality. When left untreated, OSA may result in high blood pressure, cardiovascular disease, weight gain, impotency, headaches, memory problems, job impairment, and/or motor vehicle crashes. Despite the seriousness of OSA, a general lack of awareness among the public and healthcare professionals results in the vast majority of OSA sufferers remaining undiagnosed and untreated.

There have been a number of efforts directed to treating OSA. For example, devices for electrically stimulating the soft palate to treat snoring and obstructive sleep apnea are disclosed in U.S. Pat. Nos. 5,284,161 and 5,792,067. These devices have had mixed results because they require patient adherence to a regimen of use, subject the patient to discomfort during sleep, and result in repeated arousal of the patient.

Another treatment, commonly referred to as continuous positive airway pressure (CPAP), delivers air into a patient's airway through a specially designed nasal mask or pillow. The flow of air creates positive pressure when the patient inhales to keep the airway open. CPAP is considered by many to be an effective non-surgical treatment for the alleviation of snoring and obstructive sleep apnea, however, patients complain about discomfort caused by the mask and hoses, including bloating, nasal drying, and dry eyes. As a result, patient compliance for CPAP is only about 40%.

Surgical treatments have also been used to treat OSA. One such treatment is referred to as uvulopalatopharyngoplasty, which involves removing about 2 cm of the trailing edge of the soft palate to reduce the soft palate's ability to flutter between the tongue and the pharyngeal wall. Another procedure uses a surgical laser to create scar tissue on the surface of the soft palate, which reduces the flexibility of the soft palate for reducing snoring and/or closing of the air passage. Yet another procedure, commonly referred to as cautery-assisted palatal stiffening operation (CAPSO), is an office-based procedure performed under local anesthesia whereby a midline strip of soft palate mucosa is removed, and the wound is allowed to heal whereupon the flaccid palate is stiffened.

Surgical procedures such as those mentioned above continue to have problems. More specifically, the area of tissue that is surgically treated (i.e., removal of palatal tissue or scarring of palatal tissue) is often larger than is necessary to treat the patient's condition. In addition, the above-mentioned surgical procedures are often painful with extended, uncomfortable healing periods. For example, scar tissue on the soft palate may present a continuing irritant to the patient. Furthermore, the above procedures are not reversible in the event of adverse side effects.

Another surgical procedure for treating OSA uses several braided PET cylinders that are implanted in tissue to make the tissues of the tongue or uvula more rigid and less prone to deflection. The Pillar™ Palatal Implant System sold by Restore Medical of St. Paul, Minn. consists of cylindrical-shaped elements of braided polyester filaments that are implanted in the soft palate for reducing the incidence of airway obstructions in patients suffering from mild to moderate OSA. The Pillar device has been associated with a number of adverse side effects, including extrusion of the cylindrical-shaped elements, infection, and patient discomfort.

Another implant system, sold under the trademark REPOSE™ by InfluENT of Concord, N.H., uses a titanium bone screw that is inserted into the posterior aspect of the mandible at the floor of the mouth. A loop of suture is passed through the tongue base and attached to the mandibular bone screw. The Repose™ procedure achieves a suspension or hammock of the tongue base making it less likely for the base of the tongue to prolapse during sleep. Due to the high activity of the tongue during wakefulness, however, the suture component of this device may act as a "cheese cutter" to the tongue, causing device failure and requiring subsequent removal.

Another effort for treating OSA involves creating an auxiliary airway for bypassing the clogged portion of the main airway. In one embodiment of commonly assigned U.S. patent application Ser. No. 12/182,402, filed Jul. 30, 2008, the disclosure of which is hereby incorporated by reference herein, an auxiliary airway is formed by implanting an elongated conduit beneath a pharyngeal wall of the pharynx. The elongated conduit has a proximal end in communication with a first region of the pharynx, a distal end in communication with a second region of the pharynx, and an intermediate section extending beneath the pharyngeal wall for bypassing an oropharynx region of the pharynx.

Magnets have also been used for treating OSA. For example, in one embodiment of commonly assigned U.S. patent application Ser. No. 12/183,955, filed Jul. 31, 2008, the disclosure of which is hereby incorporated by reference herein, a magnetic implant includes a bone anchor, a first magnet coupled to the bone anchor, a tongue anchor, a second magnet coupled to the tongue anchor, and a support for aligning the first and second magnets so that a repelling force is generated between the magnets for urging the second magnet away from the first magnet and toward the bone anchor. The support maintains the first magnet at a fixed distance from the bone anchor, aligns the first magnet with the second magnet, and guides movement of the first and second magnets. The magnetic implant disclosed in one or more embodiments of the '955 application does not have a hard stop so as to avoid the "cheese-cutter" effect observed when using implants having a hard stop.

In one embodiment of commonly assigned U.S. patent application Ser. No. 12/261,102, filed Oct. 30, 2008, the disclosure of which is hereby incorporated by reference herein, an implant for treating obstructive sleep apnea includes an elongated element having a central area implantable in a tongue, the elongated element including a first arm extending from a first end of the central area and a second arm extending from a second end of the central area, with the first and second arms extending through the tongue and being anchored to the inframandibular musculature.

In spite of the above advances, there remains a need for additional systems, devices and methods for treating OSA through minimally invasive approaches that provide long term results, that encourage patient compliance, and that minimize patient discomfort.

SUMMARY OF THE INVENTION

In one embodiment, a system for treating obstructive sleep apnea includes an anchoring element including scar tissue disposed in an inframandibular region of a head, and a tongue implant having at least one arm extending therefrom, whereby the tongue implant is implantable in a tongue with the at least one arm being connectable with the anchoring element for coupling the tongue implant with the anchoring element and/or the scar tissue. In one embodiment, the anchoring element includes a first implant part disposed in the inframandibular region, whereby the scar tissue is formed at least partially around the first implant part. The tongue implant is coupled with the first implant part and/or the scar tissue through the at least one arm.

In one embodiment, the first implant part includes a flexible layer such as a flexible mesh or fabric. The first implant part may be biocompatible. In one embodiment, the first implant part includes resorbable material, non-resorbable material, biocompatible mesh, biocompatible fabric, woven mesh, knitted mesh, non-woven mesh, non-knitted mesh, a braided element, polypropylene, stainless steel, nitinol, silicone, polyethylene, polytetrafluoroethylene, resorbable synthetic polymers, polylactide, polyglycolide, polydioxanone, polycaprolactone, and co-polymers thereof.

In one embodiment, the tongue implant is elongated. The tongue implant is desirably flexible. In one embodiment, the tongue implant includes a buttress that defines a larger width region of the second implant part. After being implanted in a tongue, the buttress is preferably adapted to extend along an axis that traverses an anterior-posterior axis of the tongue. In one embodiment, the buttress section extends along an axis that is substantially perpendicular to the anterior-posterior axis of the tongue. The tongue implant may include a first arm extending from a first end of the buttress and a second arm extending from a second end of the buttress. The tongue implant may also include a first set of barbs projecting from the first arm and a second set of barbs projecting from the second arm. In one embodiment, the tongue implant may include a braided element and the first and second sets of barbs may extend through interstices of the braided element.

In one embodiment, a system for treating obstructive sleep apnea includes an anchoring element including scar tissue disposed in an inframandibular region of the head, and a tongue implant implantable in a tongue, whereby the tongue implant includes a buttress and at least one arm extending from the buttress. The at least one arm of the tongue implant is preferably attachable to the anchoring element for coupling the tongue implant with the anchoring element and/or the scar tissue. In one embodiment, the at least one arm includes a first arm extending from a first end of the buttress, the first arm having a first set of barbs projecting therefrom, and a second arm extending from a second end of the buttress, the second arm having a second set of barbs projecting therefrom. The barbs projecting from the first and second arms are preferably adapted to engage the scar tissue for coupling the tongue implant and the scar tissue together. In one embodiment, the spacing between the central buttress section of the tongue implant and the scar tissue is adjustable by pulling the first and second arms through the anchoring element and/or the scar tissue. As the arms are pulled through the anchoring element and/or the scar tissue, the barbs on the arms desirably collapse inwardly for allowing the arms to pass through the anchoring element and/or scar tissue. If the arms are pulled in the opposite direction, the barbs flex outwardly so as to engage the anchoring element and/or the scar tissue so as to limit or prevent movement of the arms in the opposite direction.

In one embodiment, the tongue implant may be made of materials including monofilaments, barbed monofilaments, braided elements, barbed braided elements, sutures and barbed sutures. The anchoring element may be made of biocompatible mesh, biocompatible fabric, woven mesh, knitted mesh, non-woven mesh, non-knitted mesh, a braided element, polypropylene, stainless steel, nitinol, silicone, polyethylene, polytetrafluoroethylene, resorbable synthetic polymers, polylactide, polyglycolide, polydioxanone, polycaprolactone, and co-polymers thereof.

In one embodiment, a method of treating obstructive sleep apnea includes forming scar tissue in an inframandibular region, implanting a tongue implant in a tongue, whereby the tongue implant has at least one arm extending therefrom, and advancing the at least one arm through the tongue and toward the inframandibular region for coupling the tongue implant with the scar tissue. In one embodiment, the scar tissue is formed by implanting a flexible layer in the inframandibular region, and forming the scar tissue at least partially on, in and/or around the flexible layer. In one embodiment, a sclerosing agent may be provided on, in and/or around the flexible layer for precipitating the formation of the scar tissue. The flexible layer may include absorbable and/or non-resorbable materials. The flexible layer may also be biocompatible and may include a mesh and/or a fabric. In one embodiment, the scar tissue may be formed using energy such as heat or laser energy. In one embodiment, the scar tissue may be formed by using energy and without requiring the implantation of a flexible layer.

In one embodiment, the tongue implant desirably includes a buttress, a first arm extending from the first end of the buttress, and a second arm extending from a second end of the buttress. The buttress desirably has a larger cross-sectional width than the cross-sectional width of the first and second arms. In one embodiment, the first arm has a first set of barbs projecting therefrom and a second arm has a second set of barbs projecting therefrom. The securing step may include engaging the scar tissue with the first and second sets of barbs on the respective first and second arms. In one embodiment, at least one of the arms is coupled with the scar tissue using sutures, clips, barbs, knots and/or adhesive.

In one embodiment, the first and second sets of barbs project away from one another in opposite directions. The tongue implant may include a braided element and the first and second barbs may extend through interstices of the braided element. In one embodiment, the tongue implant may include a braided buttress having a varying cross-sectional geometry.

In one embodiment, the spacing between the buttress section of the tongue implant and the anchoring element and/or the scar tissue in the inframandibular region may be adjusted by pulling the first and second barbed arms through the anchoring element and/or the scar tissue. As the barbed arms are pulled through the anchoring element and/or the scar tissue, the barbs preferably collapse inwardly to allow the arms to advance. If the arms are then pulled in the opposite direction, the barbs will flex outwardly to hold the arms in place so as to prevent the back of the tongue from sealing the airway to cause an OSA event. In one embodiment, the anchoring element may be a first implant part implantable in an inframandibular region and the tongue implant may be a second implant part implantable in a tongue or extending through a tongue.

As used herein, the term "inframandibular region" generally refers to the geniohyoid, mylohyoid, digastrics and pterygoid muscles, and may also include any tissue surrounding those muscle groups. Tension is preferably applied to the first and second arms for pulling the center area of the tongue implant toward the inframandibular musculature, which, in turn, moves a posterior surface of the tongue away from an opposing surface of a pharyngeal wall. In one embodiment, after the tension is applied, the first and second arms are desirably anchored to the anchoring element and/or the scar tissue in the inframandibular region for maintaining a space between the posterior surface of the tongue and the opposing surface of the pharyngeal wall.

In one embodiment, the braided arms may be modified to include barbed elements projecting therefrom so as to enhance anchoring of the arms in tissue upon implantation. In one embodiment, needles may be secured to the distal ends of the arms. A barbed element may be placed in the core of the braid or the braid may be formed around the barbed element. In one embodiment, the barbs preferably exit through the interstices of the braid so as to provide for enhanced tissue fixation to the hyoid bone, thyroid cartilage, scar tissue, tongue tissue, and/or other tissues such as muscles or fascia in the inframandibular region. In one embodiment, the barbs may serve as a means for attaching the implant device to additional components implanted in inframandibular musculature and/or soft tissue or cartilage located near the inframandibular musculature.

In one embodiment scar tissue is formed in the inframandibular region. The scar tissue may be formed by implanting a first implant part or an anchoring element in the inframandibular region. The scar tissue may also be formed using energy such as laser energy or heat, or by using a sclerosing agent. After the scar tissue is formed, a second implant part such as a tongue implant or a barbed device with a buttress in the center is implanted within a patient's mouth. The procedure may be performed on an outpatient basis or require a one night hospital stay. The arms coupled with the center buttress are preferably secured to a scar tissue and/or the first implant part disposed in inframandibular musculature and/or inframandibular tissue. The distance between the buttress and the scar tissue and/or first implant part may be adjusted by a surgeon at the time of implantation and will serve to prevent the tongue from sealing against the posterior wall of the pharynx. In one embodiment, by securing the arms to a soft anchor disposed in the inframandibular region, the "cheese cutter" effect that occurs when anchoring to a hard stop is avoided.

In one embodiment, the materials used for forming the tongue implant and/or the second implant part may include biocompatible materials such as non-resorbable and resorbable polymers. Suitable non-resorbable polymers may include silicone, polyethylene terephalate, polytetrafluoroethylene, polyurethane and polypropylene. Suitable resorbable polymers may include polylactide, polyglycolide copolymers, polycaprolactone, and collagen. In addition, materials such as nitinol, stainless steel, or resorbable alloys such as magnesium or iron alloys may be used to form the second implant part. In one embodiment, bladders of electrorheologic or magnetorheologic materials may also be placed within the center of the tongue implant and/or the second implant part. The stiffness of these materials may be altered by placing a magnet or electric field at a desired location such as in the soft palate or the posterior pharyngeal wall. The necessary magnetic or electric field may be applied by an external source and may be transmitted percutaneously to the materials by inductive coupling.

In one embodiment, an anchoring element is disposed in an inframandibular region and the anchoring element is coupled with a hyoid bone using one or more tethers or arms that are coupled with the hyoid bone. The length of the tether(s) or arm(s) may be adjusted for shifting the hyoid bone in an anterior direction. In one embodiment, the anchoring element includes a flexible layer and/or scar tissue.

These and other preferred embodiments of the present invention will be described in more detail below.

BRIEF DESCRIPTION OF THE DRAWING

FIG. 4A shows a system for treating obstructive sleep apnea including a first implant part implantable in inframandibular tissue, in accordance with one embodiment of the present invention.

FIG. 4B shows a system for treating obstructive sleep apnea including the first implant part implantable in inframandibular tissue and a second implant part implantable in a tongue, in accordance with one embodiment of the present invention.

FIG. 9 shows an implant system for treating obstructive sleep apnea, in accordance with one embodiment of the present invention.

FIG. 10 shows an implant system for treating obstructive sleep apnea, in accordance with one embodiment of the present invention.

DETAILED DESCRIPTION

Figure 1:
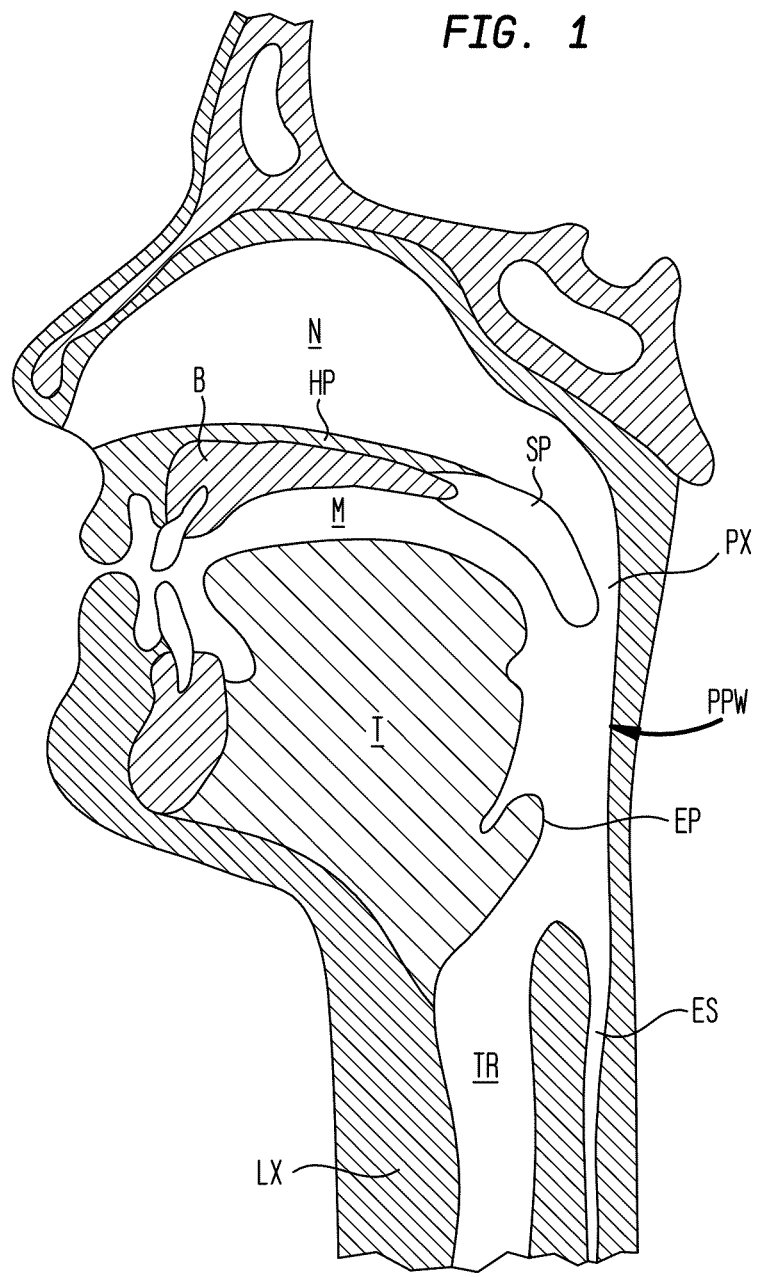
FIG. 1 shows a cross-sectional view of a human head including a nasal cavity and a pharynx.

FIG. 1 shows a cross-section of a human head with anatomical structures including the nasal cavity N, bone B of the hard palate HP, the soft palate SP, the mouth M, the tongue T, the trachea TR, the epiglottis EP, the esophagus ES, and the posterior pharyngeal wall PPW. In the human head, an air filled space between the nasal cavity N and the larynx LX is referred to as the upper airway. The most critical part of the upper airway associated with sleep disorders is the pharynx PX.

Figure 2:
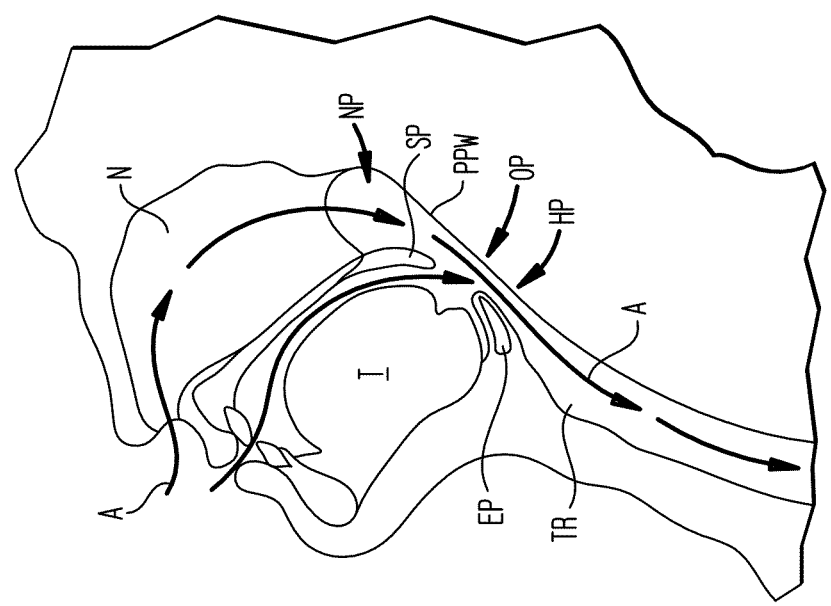
FIG. 2 shows a cross-sectional view of the nasal cavity and the pharynx of a human during normal breathing.

Referring to FIG. 2, the pharynx has three different anatomical levels. The nasopharynx NP is the upper portion of the pharynx located in the back of the nasal cavity N. The oropharynx OP is the intermediate portion of the pharynx containing the soft palate SP, the epiglottis EP, and the curve at the back of the tongue T. The hypopharynx HP is the lower portion of the pharynx located below the soft tissue of the oropharynx OP. The oropharynx OP is the section of the pharynx that is most likely to collapse due to the high prevalence of soft tissue structure, which leaves less space for airflow. The hypopharynx HP lies below the aperture of the larynx and behind the larynx, and extends to the esophagus.

As is well known to those skilled in the art, the soft palate and the tongue are both flexible structures. The soft palate SP provides a barrier between the nasal cavity N and the mouth M. In many instances, the soft palate SP is longer than necessary and extends a significant distance between the back of the tongue T and the posterior pharyngeal wall PPW.

Although the muscles relax throughout the body during sleep, most of the muscles of the respiratory system remain active. During inhalation, the diaphragm contracts and causes negative pressure to draw air A into the nasal cavity N and the mouth M. The air then flows past the pharynx PX, through the trachea TR and into the lungs. The negative pressure causes the tissue of the upper airway to deform slightly, which narrows the airway passage. In apneic patients, the soft palate SP, the tongue T, and/or the epiglottis EP collapse against the posterior pharyngeal wall PPW to block airflow into the trachea. As the airway narrows, airflow through the pharynx becomes turbulent which causes the soft palate SP to vibrate, generating a sound commonly known as snoring.

During sleep, humans typically experience brief obstructions of airflow and/or small decreases in the amount of airflow into the trachea and lungs. An obstruction of airflow for more than ten seconds is referred to as apnea. A decrease in airflow by more than fifty percent is referred to as hypopnea. The severity of sleep disorders is measured by the number of apneas and hypopneas that occur during every hour of sleep.

If apnea or hypopnea occurs more than five times per hour, most medical personnel diagnose the individual as having an upper airway resistance problem. Many of these patients often exhibit symptoms related to sleep disorders including sleepiness during the day, depression, and difficulty concentrating.

Individuals having ten or more episodes of apnea or hypopnea during every hour of sleep are officially classified as having obstructive sleep apnea syndrome. As the airway is obstructed, the individual makes repeated attempts to force inhalation. Many of these episodes are silent and are characterized by movements of the abdomen and chest wall as the individual strains to draw air into the lungs. Typically, episodes of apnea may last a minute or more. During this time, oxygen levels in the blood will decrease. Ultimately, the obstruction may be overcome by the individual generating a loud snore or awakening with a choking feeling.

Referring to FIG. 2, when an individual is awake, the back of the tongue T and the soft palate SP maintain their shape and tone due to their respective internal muscles. As a result, the airway A through the pharynx remains open and unobstructed. During sleep, however, the muscle tone decreases and the posterior surface of the tongue and the soft palate become more flexible and distensible.

Figure 3:
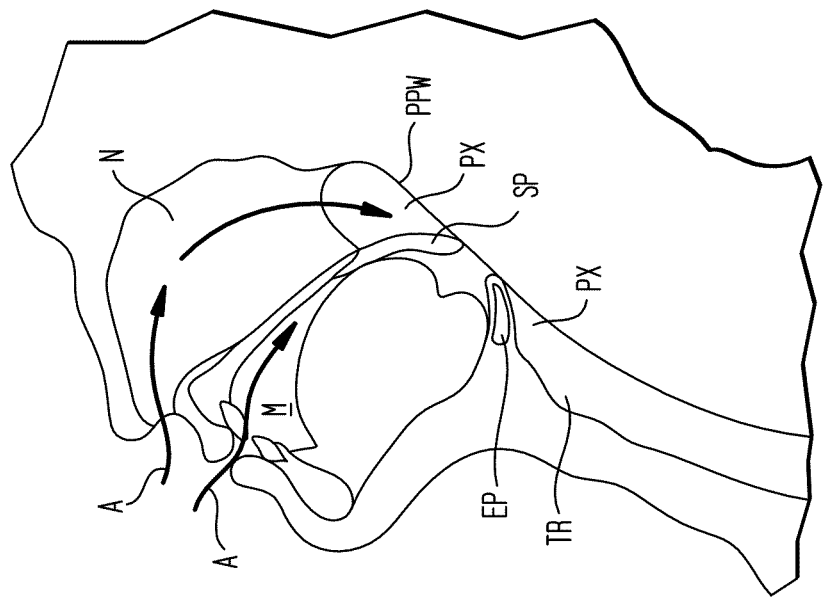
FIG. 3 shows a cross-sectional view of the nasal cavity and the pharynx of a human having an airway that is at least partially closed.

Referring to FIG. 3, without normal muscle tone to keep their shape and to keep them in place either alone or as a group, the posterior surface of the tongue T, the epiglottis EP, and the soft palate SP tend to easily collapse to block the airway A.

Referring to FIG. 4A, in one embodiment of the present invention, an implant 20 used for treating obstructive sleep apnea includes a first implant part 22 or anchoring element implantable in an inframandibular region IR of a head. In one preferred embodiment, the first implant part 22 is implantable between tissue planes in the inframandibular region IR. In a more preferred embodiment, the first implant part 22 is implanted between geniohyoid musculature and mylohyoid musculature. The first implant part 22 desirably includes a biocompatible, flexible pad such as a mesh or fabric pad, a woven or knitted mesh, a non-woven or non-knitted mesh, a flat braid comprised of polypropylene or any combination of the above materials. The first implant part 22 may also be made of stainless steel, nitinol, silicone, polyethylene, or polytetrafluoroethylene, and/or resorbable synthetic polymers such as polylactide, polyglycolide, polydioxanone, polycaprolactone, or co-polymers thereof. The first implant part may include a film having openings, pores, or perforations for enabling tissue ingrowth, or may include a resorbable film having non-resorbable particles or fibers that precipitate the formation of scar tissue. A sclerosing agent may be used in combination with the first implant part to encourage the formation of scar tissue on, in and/or around the first implant part. Energy such as laser energy or heat may also be used to form the scar tissue in the inframandibular region. The scar tissue desirably provides a soft tissue anchor in the inframandibular region of an oral cavity. In one embodiment, the scar tissue is preferably a scar plane or scar plate that lies in the inframandibular region. In one embodiment, the anchoring element provided in the inframandibular region may only include scar tissue that is formed without requiring the implantation of a first implant part.

In one embodiment, the first implant part or anchoring element includes a mesh or fabric pad having a sclerosing agent provided thereon that is implanted in the inframandibular region. The mesh or fabric pad is left in place as scar tissue forms at least partially on, in and/or around the mesh or fabric pad. After a period of time, the newly formed scar tissue defines a mass of scar tissue such as a scar plane or scar plate that is disposed in the inframandibular region. The scar tissue preferably provides a soft anchor in the inframandibular region that may be coupled with an implant part disposed in a tongue, or coupled with a hyoid bone.

In one embodiment, the first implant part 22 has a size and shape that may be modified by a surgeon at the time of implantation. In one embodiment, a square of biocompatible mesh or fabric has dimensions of about four inches in length and about four inches in width. During surgery, the surgeon may cut the mesh or fabric into a size and shape reflecting the surgical needs of a patient, such as a rectangle, square, elliptical, or surgical shape.

Referring to FIG. 4B, in one embodiment of the present invention, the implant 20 includes a second implant part 24 implantable in a tongue T. The second implant part 24 may be elongated and may include a filament, a braided tube, or a braided barbed tube having a first end 26 and a second end 28. The second implant part 24 preferably includes a buttress section 30 at a center portion thereof. The second implant part 24 also desirably includes a first arm 32 extending between the buttress section 30 and the first end 26, and a second arm 34 extending between the buttress section 30 and the second end 28. The buttress section 30 desirably forms the widest and/or largest diameter portion of the second implant part 24, and desirably has a greater width and/or diameter than the diameter of the respective first and second arms 32, 34. The wider buttress section 30 preferably provides enhanced anchoring of the second implant part 24 in the tissue of the tongue T, and minimizes the likelihood of movement of the second implant part in the tongue.

In one embodiment, the first and second arms 32, 34 projecting from the buttress may have barbs. The barbs desirably enhance attachment of the first and second arms of the second implant part to the first implant part and/or the scar plane formed about the first implant part. In one embodiment, the barbs on the respective first and second arms project in opposite directions.

In one or more preferred embodiments, the second implant part 24 may be formed from non-absorbable materials, absorbable materials, or a combination of non-absorbable and absorbable materials. The non-absorbable materials may include polymeric materials such as non-resorbable polymers, silicone, polyethylene terephalate, polytetrafluoroethylene, polyurethane and polypropylene, nitninol, stainless steel, and/or composite materials. Suitable resorbable polymers may include polylactide, polyglycolide copolymers, polycaprolactone, and/or collagen.

The first implant part 22 preferably serves as a "soft anchor" for the second implant part positioned in the tongue. In one embodiment, the spacing between the first implant part 22 and the second implant part 24 may be adjusted by pulling the first and second arms 32, 34 of the second implant part toward the first implant part so as to shorten the length of the arms between the two implant parts. The second implant part in the tongue is preferably advanced in an anterior and/or inferior direction so as to prevent the tongue from sealing against the back wall of the pharynx. The arms are preferably secured to the first implant part so as to maintain the tongue in the forward shifted position. The distal ends 26, 28 of the first and second arms 32, 34 are preferably secured to the first implant part 22 using methods and devices that are described in more detail herein.

Figure 5A:
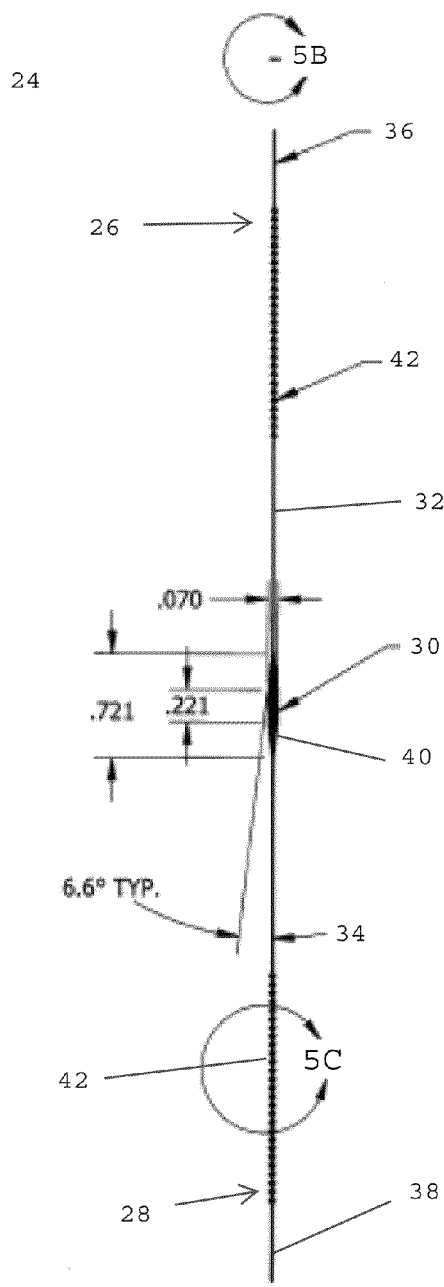
FIGS. 5A-5C show the second implant part of FIG. 4B, in accordance with one embodiment of the present invention.

Referring to FIG. 5A, in one embodiment, the second implant part 24 or tongue implant desirably includes the first end 26 and the second end 28. The elongated second implant part 24 preferably includes the buttress section 30 at the center portion thereof, the first arm 32 located between the buttress section 30 and the first end 26, and a first needle 36 secured to the free end 26 of the first arm 32. The second implant part 24 also preferably includes the second arm 34 extending between the buttress section 30 and the second end 28 thereof, and a second needle 38 secured to the free end 28 of the second arm 34. In one embodiment, the buttress section 30 desirably forms the widest and/or largest diameter portion of the second implant part 24 so that the buttress section 30 has a width or diameter that is greater than the width or diameter of the respective first and second arms 32, 34.

Figure 5B:
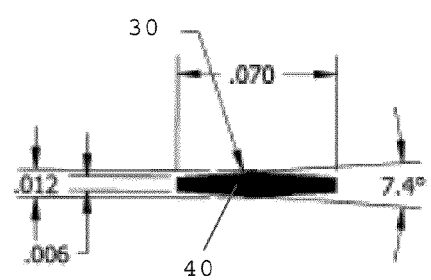

Referring to FIGS. 5A and 5B, in one embodiment, the buttress section 30 of the second implant part 24 desirably includes a biocompatible element 40 disposed therein. In one embodiment, the biocompatible element 40 may be placed within a previously implanted second implant part or may be inserted into the center of the second part before implanting the second implant part in tissue. The biocompatible element 40 may have an elliptical shape and may also comprise a biocompatible metal or alloy.

Figure 5C:
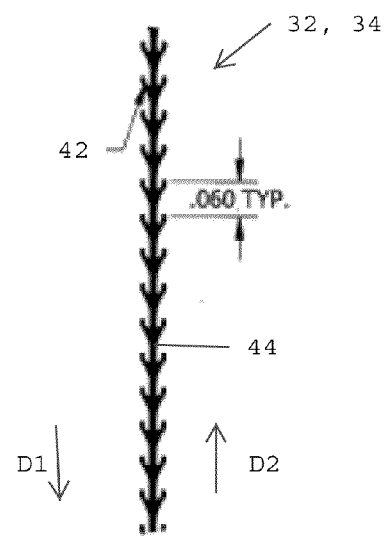

Referring to FIG. 5C, in one embodiment, one or more of the first and second arms 32, 34 preferably includes a plurality of barbs 42 that project from a flexible core 44. The plurality of barbs 42 are desirably spaced from one another along the length of the flexible core 44. In one embodiment, the tips of sequentially positioned barbs 42 are about 0.060 inches from one another. In one embodiment, the barbs 42 are adapted to collapse inwardly when pulled through tissue in a first direction designated $D_1$, and to engage the tissue for holding the first and second arms 32, 34 in place when pulled in a second direction designated $D_2$. In one embodiment, the base portions of the barbs 42 may be staggered along the axis of each arm 32, 34 to either partially oppose each other or to prevent direct opposition of any two barbs along the axis of each arm 32, 34.

Figures 6A, 6B:
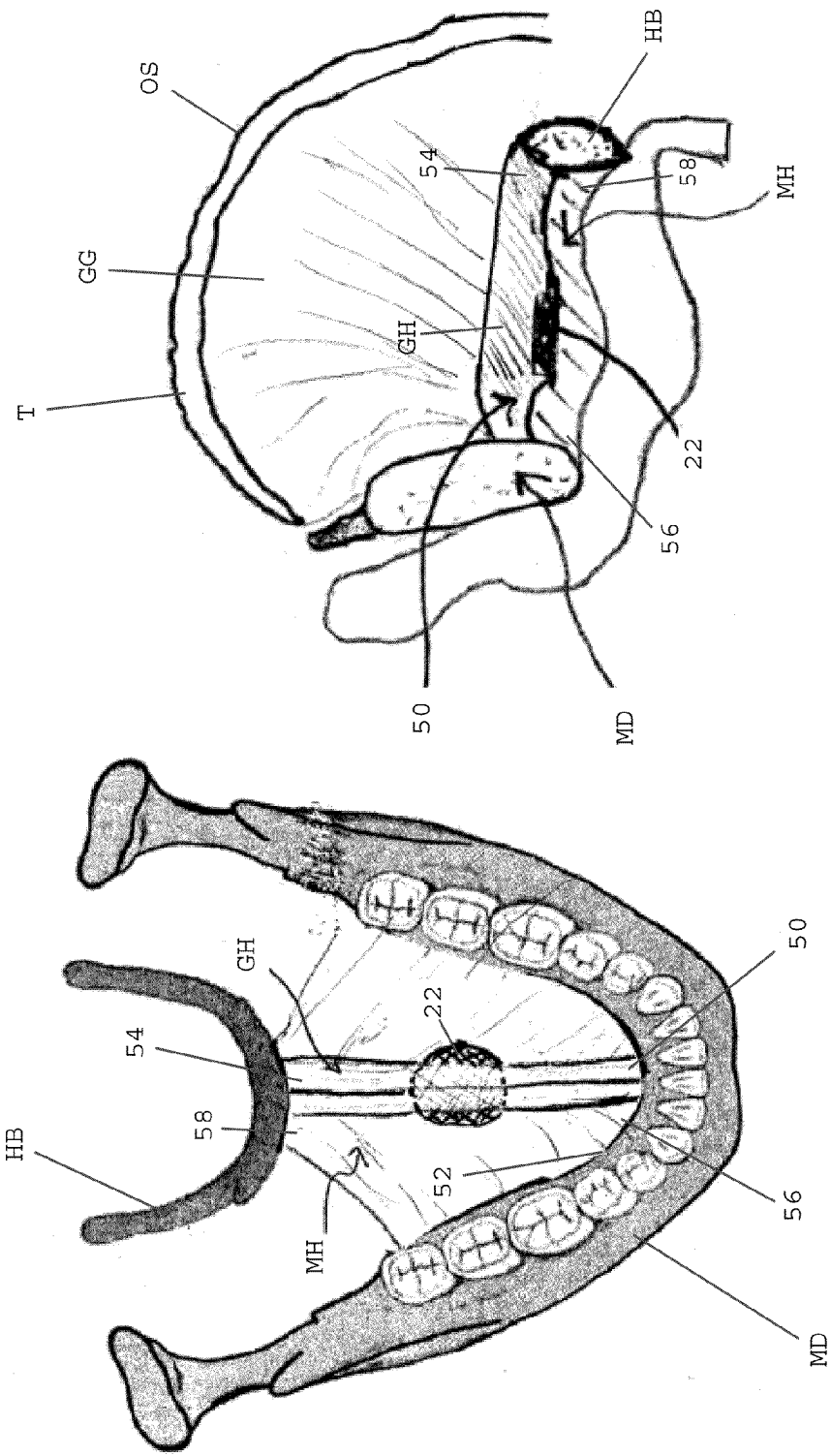
FIGS. 6A and 6B show a method of treating obstructive sleep apnea including implanting a first implant part in an inframandibular region, in accordance with one embodiment of the present invention.

Referring to FIGS. 6A and 6B, in one embodiment, an oral cavity of a patient includes a mandible MD, a hyoid bone HB, geniohyoid musculature GH, and mylohyoid musculature MH. The geniohyoid musculature GH has an anterior end 50 connected to an inner surface 52 of the mandible MD, and a posterior end 54 connected to the hyoid bone HB. The mylohyoid musculature MH has an anterior end 56 that is coupled with the inner surface 52 of the mandible MD and a posterior end 58 connected with the hyoid bone HB. The oral cavity also includes the tongue T (FIG. 6B) having genioglossus musculature GG and an outer surface OS.

Referring to FIGS. 6A and 6B, in one embodiment, the first implant part 22 or anchoring element shown and described above is implanted in inframandibular tissue and more preferably between the geniohyoid musculature GH and the mylohyoid musculature MH. In one embodiment, the first implant part 22 is a porous layer that allows for tissue ingrowth (e.g. scar tissue) into the layers. In one embodiment, the first implant part 22 is preferably implanted between the geniohyoid musculature GH and the mylohyoid musculature MH as part of a first phase of a surgical procedure. After the first implant part 22 is implanted, the first implant part 22 is left in place so that scar tissue may form in and/or around the first implant part. The scar tissue that forms in and/or around the first implant part preferably forms a scar plane or scar plate extending between the geniohyoid musculature GH and the mylohyoid musculature MH. The scar plane or scar plate desirably forms a soft anchor for a second implant part positioned in a tongue, as will be described in more detail below. The first implant part may be resorbed as the scar tissue forms.

Figures 7A, 7B:
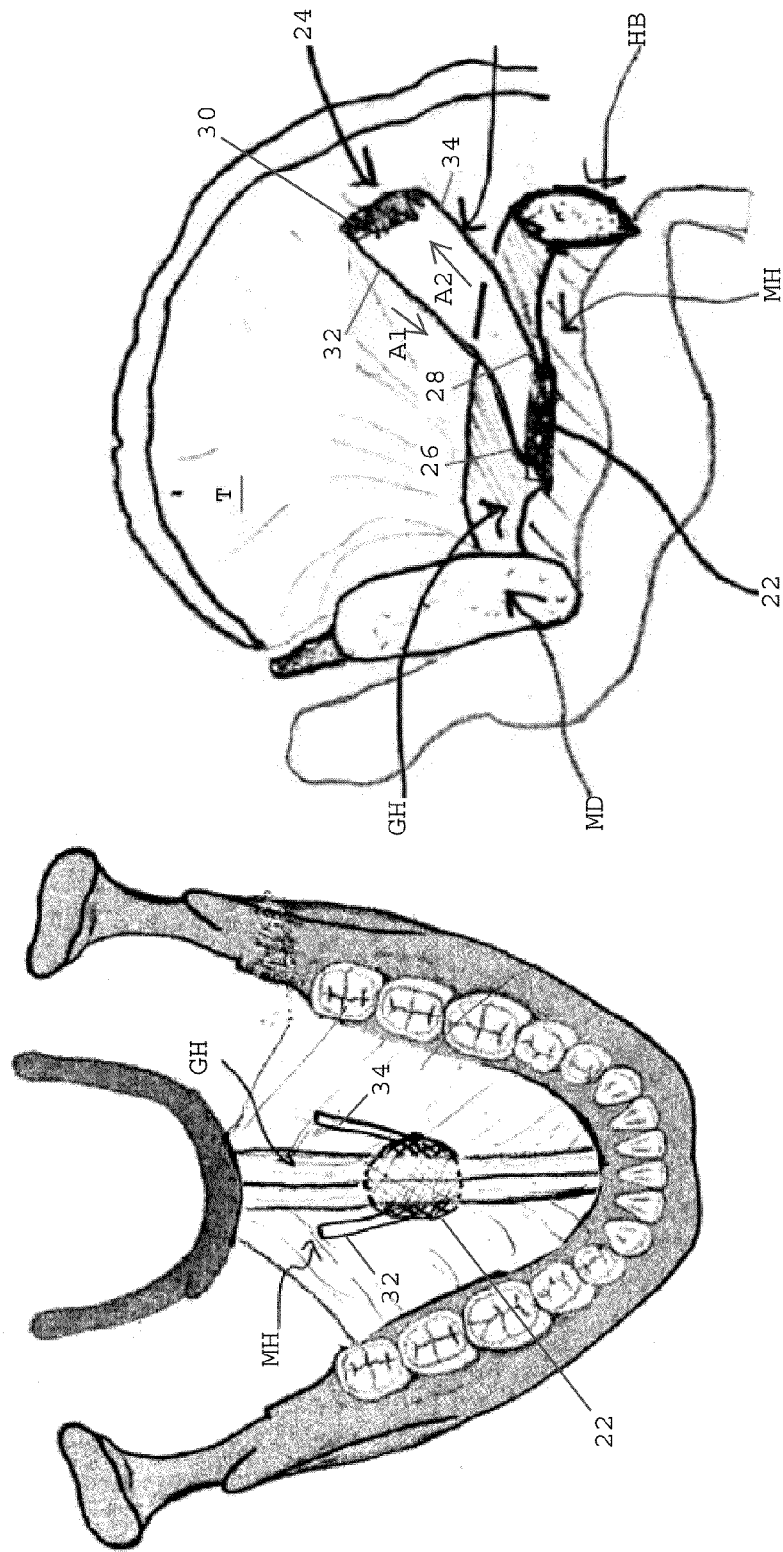
FIGS. 7A and 7B show a method of treating obstructive sleep apnea including implanting a second implant part in a tongue, in accordance with one embodiment of the present invention.

Referring to FIGS. 7A and 7B, after the first implant part 22 has been implanted between the geniohyoid musculature GH and the mylohyoid musculature MH, and after scar tissue (e.g. a scar plane) has been allowed to form about the first implant part 22, a second implant part 24, such as that shown and described above in FIGS. 4B and 5A-C, may be connected with the first implant part 22 and/or the scar tissue that has formed around the first implant part.

In one embodiment, a surgeon may adjust the length of the respective first and second arms 32, 34 to shift the tongue T in an anterior and/or inferior direction so as to minimize the possibility of OSA episodes. In one embodiment, the first and second arms 32, 34 desirably include barbs that enable the first and second arms to be advanced through the interstices or pores of the first implant part 22 and/or the scar tissue in the inframandibular region. The barbs preferably enable the arms to move more easily in the direction designated $D_1$, while providing more resistance to movement when the arms are pulled in the direction designated $D_2$.

Figure 8A:
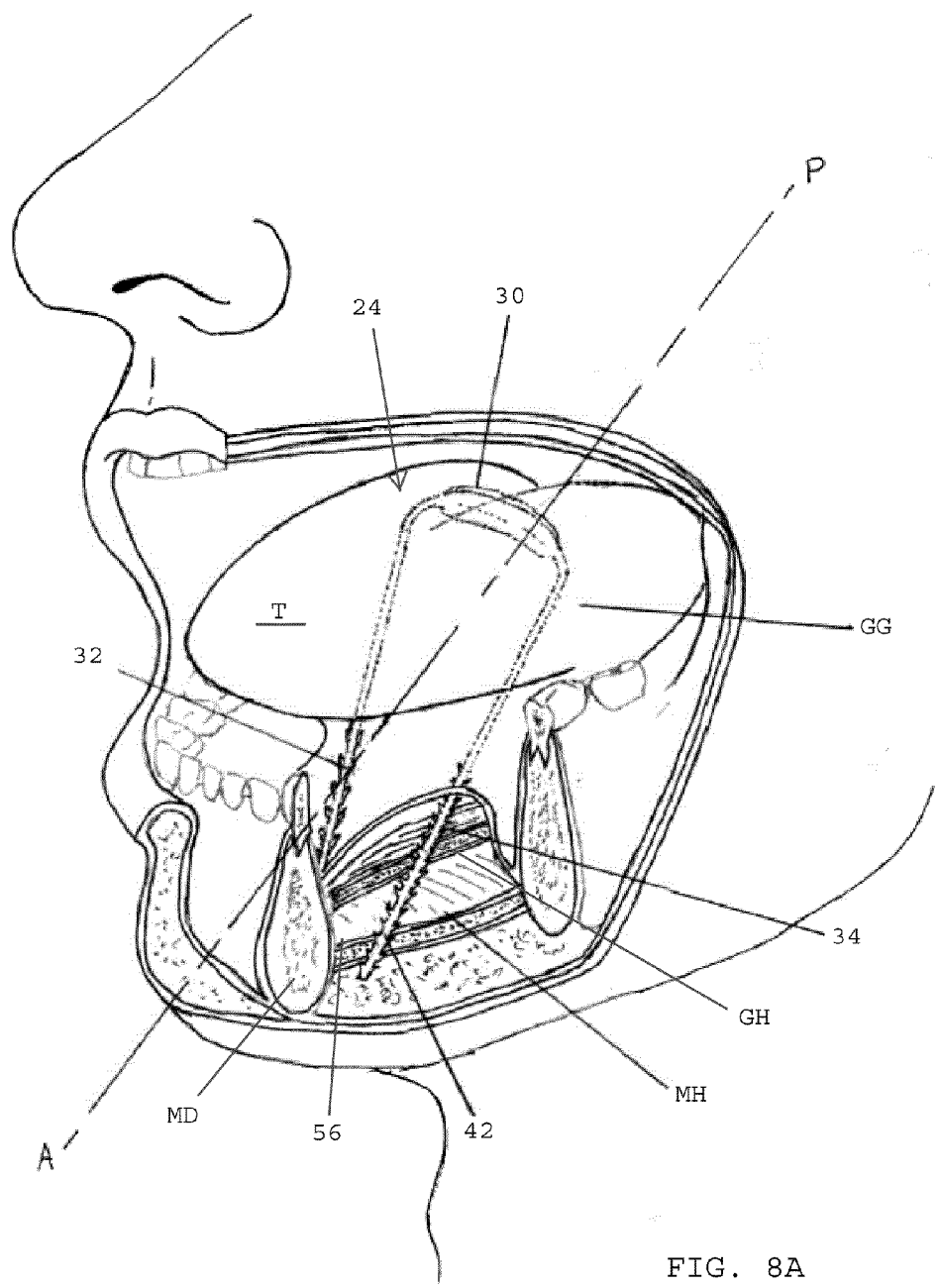
FIGS. 8A and 8B show the second implant part of FIGS. 5A-5C implanted in a tongue, in accordance with one embodiment of the present invention.
Figure 8B:
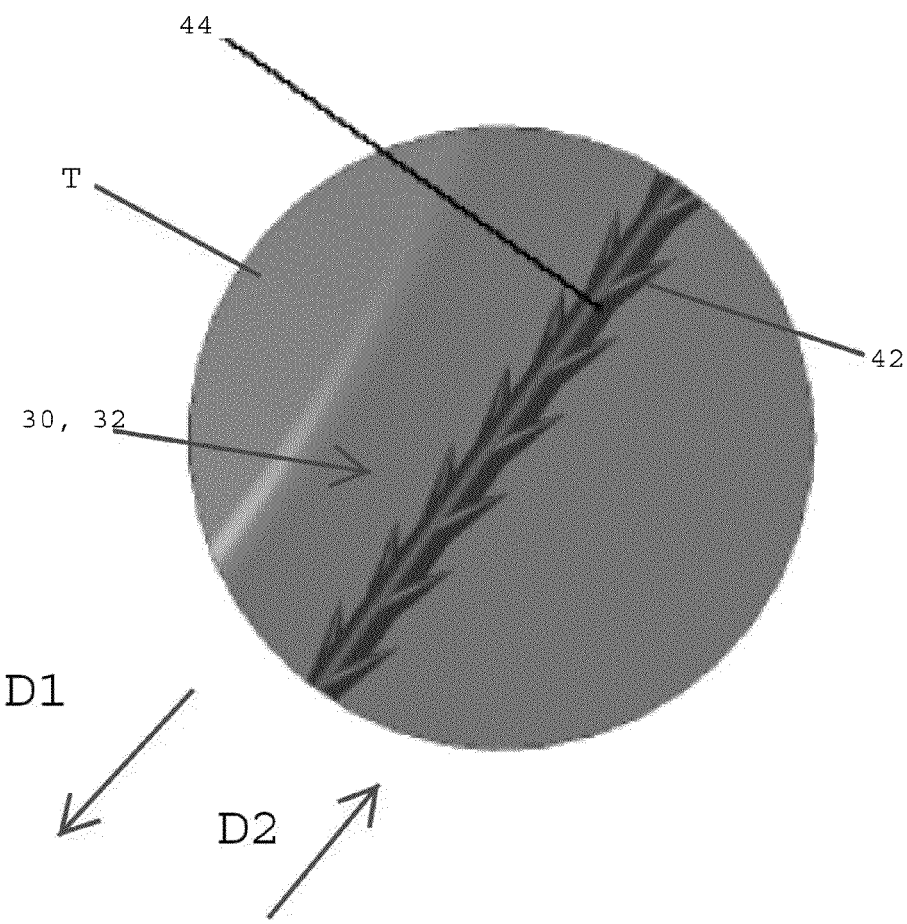

Referring to FIGS. 8A and 8B, in one embodiment, the second implant part 24 or tongue implant is preferably positioned within the tongue T so that the buttress section 30 is located in the center of the tongue body and extends laterally toward the sides of the oral cavity. In one embodiment, the buttress section 30 extends along an axis that traverses or is substantially perpendicular with an anterior-posterior axis (designated A-P) of the tongue T. In one embodiment, the buttress section 30 preferably has a larger surface area than other sections of the second implant part 24 for anchoring the second implant part in place and for avoiding the "cheese cutter" effect present when using implants with immovable anchor positions (e.g. bone anchors), or implants having a relatively small diameter filament implanted in the tongue. In one embodiment, first and second arms 32, 34 of the second implant part 24 are desirably advanced from the buttress section 30 thereof toward the anterior end 56 of the mylohyoid muscle MH.

Referring to FIG. 8B, in one embodiment, one or more of the first and second arms 32, 34 extending through the tissue of the tongue T preferably includes a flexible core 44 and a plurality of barbs 42 projecting outwardly from the flexible core 44. The barbs 42 preferably collapse inwardly toward the core 44 as the arms 32, 34 are pulled in a first direction designated $D_1$. The barbs 42 project outwardly when the arms 32, 34 are pulled in an opposite second direction designated $D_2$ for holding the arms 32, 34 in place in the tissue of the tongue T. Although the present invention is not limited by any particular theory of operation, it is believed that the barbs 42 enhance anchoring of the second implant part 24 in tissue and enhance securing the arms 32, 34 of the second implant part to the first implant part and/or the scar tissue in the inframandibular region.

In one embodiment, one or more barbed elements are placed within the core of an elongated second implant part or tongue implant. In one preferred embodiment, the barbed elements are placed within the core of a braided tube and/or a braided tube may be formed about one or more barbed elements. In one embodiment, barbs preferably project through interstices of a braided element so as to enable enhanced tissue fixation. In one embodiment, needles are secured to the respective distal ends of the arms for advancing the arms through tissue, muscle, cartilage, or scar tissue. In one embodiment, the needles may be passed through the thyroid cartilage of a patient.

Referring to FIG. 5, in one embodiment, the center buttress section 30 of the second implant part 24 is adapted to be implanted into the base of the posterior tongue T near the oropharynyx, and the free ends of the first and second arms 32, 34 are adapted to be connected to the first implant part 22 and/or scar tissue disposed in the inframandibular region. As noted above, the center buttress section 30 of the second implant part 24 is desirably expanded at the point that is implanted in the tongue.

Referring to FIG. 9, in one embodiment, a system for treating OSA includes a first implant part 122 or anchoring element implanted in an inframandibular region of a head such as being disposed between geniohyoid musculature GH and mylohyoid musculature MH. The first implant part 122 may be a flexible or compliant biocompatible mesh or fabric that desirably precipitates the formation of scar tissue or a scar plane SP about the first implant part 122. A sclerosing agent may be used with the first implant part to encourage the growth of scar tissue. After implantation between the geniohyoid musculature GH and the mylohyoid musculature MH, the first implant part 122 is preferably left in place as the scar tissue forms about the first implant part 122. The first implant part may be resorbable as the scar tissue forms. A second implant part 124, such as a second implant part having one or more of the features shown in FIGS. 5A-5C, may be coupled with the hyoid bone HB of a patient. The second implant part 124 desirably includes an anchor 125, and a tether 132 having an anterior end 126 coupled with the first implant part 122 and a posterior end 127 coupled with the anchor 125. The tether 132 may include barbs for attaching the tether 132 to the first implant part 122 or scar tissue. The length of the tether 132 may be adjusted for advancing the hyoid bone HB in the anterior and/or inferior direction designated $A_1$. As the hyoid bone HB is moved in the anterior and/or inferior direction designated $A_1$, the posterior surface of the tongue is preferably shifted anteriorly and/or inferiorly for spacing a posterior surface of the tongue from an opposing pharyngeal wall for minimizing the likelihood of OSA events.

Referring to FIG. 10, in one embodiment, a system for treating OSA desirably includes a first implant part 222 or anchoring element, such as flexible mesh or porous fabric, implanted between geniohyoid musculature GH and mylohyoid musculature MH. After implantation of the first implant part 222, the first implant part is maintained between the geniohyoid musculature GH and the mylohyoid musculature MH so that a scar plane SP may form about the first implant part 222. After the scar plane SP has been formed, tethers 232, 234 may be used for coupling the scar plane with a hyoid bone HB. The first tether 232 desirably has an anterior end 226 attached to the first implant part 222 and/or scar tissue, and a posterior end 227 coupled with the hyoid bone HB. In one embodiment, the posterior end 227 of the first tether 232 is wrapped around the hyoid bone HB at least once. In one preferred embodiment, the posterior end 227 of the first tether 232 is wrapped around the hyoid bone HB multiple times. The implant system also includes the second tether 234 having an anterior end 228 attached to the first implant part 222 and/or scar tissue, and a posterior end 229 anchored to the hyoid bone HB. As above, the posterior end 229 of the second tether 234 is desirably wrapped around the hyoid bone HB one or more times.

Referring to FIGS. 6A-6B and 7A-7B, in one embodiment, one or more of the implant systems described herein may be implanted by preparing the patient for surgery using local or general anesthesia. A surgeon may implant the first implant part 22 in a plane extending between the geniohyoid muscles GH and mylohyoid muscles MH. The geniohyoid and mylohyoid muscles are desirably exposed by making a small incision in a tissue fold under the mandible MD. Scar tissue may form around the first implant part. The first implant part and/or the scar tissue that forms desirably provide a soft anchor in the inframandibular region. A second implant part, such as a tongue anchor or an implant coupled with a hyoid bone, may be coupled with the first implant part or the scar tissue for shifting the tongue away from an opposing pharyngeal wall for minimizing OSA events.

In one embodiment, the second implant part or tongue implant is implanted by advancing first and second arms 32, 32 of the second implant part 24 in lateral directions through the rear of the tongue T until the buttress section 30 of the second implant part 24 is centered in the tongue T. Advancement of the first and second arms is preferably facilitated by attaching tissue piercing elements such as needles to the free ends of both arms. In one embodiment, a small diameter trocar is desirably advanced through the musculature and into the floor of the mouth near the base of the tongue. A snare may be introduced through the lumen of each trocar to grab the distal ends 24, 26 of the respective first and second arms 30, 32. The first and second arms 30, 32 are pulled through the trocar and the trocar is removed. The free ends 26, 28 of the first and second arms 32, 34 are desirably pulled until the back of the tongue T is advanced just enough so that it does not form a seal against the back wall of the pharynx. The first and second arms 32, 34 may be attached to the first implant part 22 and/or the scar tissue to set the tongue in the new position. In embodiments where the first implant part is resorbable and in which the scar tissue is formed without using an implant, the first and second arms may also be attached to scar tissue formed in the inframandibular region. By securing the first implant part 22 in soft tissue such as the plane between the geniohyoid GH and the mylohyoid MH muscles, the "cheese-cutter" effect found in tongue implants having hard stops (e.g. a bone anchor) is avoided. The first and second arms 32, 34 of the second implant part 24 may be attached to the first implant part and/or scar tissue using sutures, glue, toggles, ultrasonic welding, interference with barbed elements, or direct knotting of the elongated second implant part 24 with the first implant part 22 or the scar tissue.

In one embodiment, the second implant part is fabricated as a tapered hollow braided shell through which the free ends of the first and second arms are passed. Once the tongue is set into the proper position, the large end of the flexible tube is passed over the free ends of the first and second arms. The small diameter end of the tube is pushed upward in the direction of the tongue in engagement with the barbed element. As the tube collapses and the small diameter end of the tube is pressed against the large diameter end, the collapsed mass of the tube serves as a load-bearing element against the surrounding soft tissue. Although this particular embodiment is not limited by any particular theory of operation, it is believed that the above-described structure provides an infinite number of anchoring locations or points for each distal end of the first and second arms of the first part of the implant.

In one embodiment, techniques well known to those skilled in the art are used for forming scar tissue in the inframandibular region. In one embodiment, laser energy may be used for forming the scar tissue. In another embodiment, heat energy may be used for forming the scar tissue. A sclerosing agent may also be used. An implant such as a tongue implant may be coupled with the scar tissue for shifting the position of the tongue for minimizing OSA events. A hyoid bone may also be coupled with the scar tissue using one or more elongated elements such as a tether.

The present invention provides a number of advantages over prior art methods and devices used for treating obstructive sleep apnea syndrome and hypopnea. First, the systems, devices and methods disclosed herein provide simple surgical procedures that are minimally invasive. Typically, the systems, devices and methods disclosed herein may be utilized during an outpatient procedure. In addition, the systems, devices and methods disclosed herein provide both immediate and long term results for treating obstructive sleep apnea syndrome and hypopnea. Moreover, the systems, devices and methods disclosed herein do not require a significant level of patient compliance.

In addition, the present invention does not anchor the posterior aspect of the tongue to a fixed, hard structure. Rather, the present invention uses a soft anchor in the inframandibular region. Thus, the present invention is significantly less likely to affect swallowing or speech, thereby providing a great improvement over prior art devices, systems and methods. The present invention also avoids the "cheese-cutter" effect found with prior art implants by teaching, inter alia, the use of a soft anchor in the inframandibular region and a buttress for the tongue implant. The present invention also preferably uses materials having long-term biocompatibility.

Although various embodiments disclosed herein relate to use in humans, it is contemplated that the present invention may be used in all mammals, and in all animals having air passages. Moreover, the systems, devices, and methods disclosed herein may incorporate any materials that are biocompatible, as well as any solutions or components that minimize rejection, enhance tissue ingrowth, enhance the formation of mucosal layers, and improve acceptance of the device by a body after the device has been implanted.

The headings used herein are for organizational purposes only and are not meant to be used to limit the scope of the description or the claims. As used throughout this application, the word "may" is used in a permissive sense (i.e., meaning having the potential to), rather than the mandatory sense (i.e., meaning must). Similarly, the words "include", "including", and "includes" mean including but not limited to. To facilitate understanding, like reference numerals have been used, where possible, to designate like elements common to the figures.

While the foregoing is directed to embodiments of the present invention, other and further embodiments of the invention may be devised without departing from the basic scope thereof. As such, the scope of the present invention is to be limited only as set forth in the appended claims.

What is claimed is:

1. A system for treating obstructive sleep apnea comprising:
   an anchoring element adapted to be embedded in soft tissue of an inframandibular region; and
   a tongue implant having at least one arm extending therefrom, wherein said tongue implant is implantable in a tongue with said at least one arm being connectable with said anchoring element for coupling said tongue implant with said anchoring element, and wherein spacing between said tongue implant and said anchoring element is adjustable by pulling said at least one arm through said anchoring element, wherein said anchoring element comprises a first implant part adapted to be disposed between tissue planes in the inframandibular region and said tissue at least partially surrounds said first implant part, wherein said tongue implant is coupled with said first implant part through said at least one arm, and wherein said first implant part comprises a biocompatible mesh or a biocompatible fabric.

2. The system as claimed in claim 1, wherein said tongue implant is elongated.

3. The system as claimed in claim 2, wherein said tongue implant comprises a buttress defining a larger width region of said tongue implant.

4. The system as claimed in claim 3, wherein said at least one arm comprises a first arm extending from a first end of said buttress and a second arm extending from a second end of said buttress, wherein the spacing between said buttress of said tongue implant and said anchoring element is adjustable by pulling said first and second arms through said anchoring element.

5. The system as claimed in claim 4, further comprising:
   a first set of barbs projecting from said first arm; and
   a second set of barbs projecting from said second arm.

6. The system as claimed in claim 5, wherein said tongue implant comprises a braided element and said first and second sets of barbs extend through interstices of said braided element.

7. The system as claimed in claim 3, wherein said buttress is adapted to extend along an axis that traverses an anterior-posterior axis of said tongue.

8. The system as claimed in claim 1, wherein said first implant part comprises a flexible layer adapted to be implanted between geniohyoid musculature and mylohyoid musculature in the inframandibular region.

9. The system as claimed in claim 1, wherein said first implant part comprises materials selected from the group consisting of resorbable material, non-resorbable material, biocompatible mesh, biocompatible fabric, woven mesh, knitted mesh, non-woven mesh, non-knitted mesh, a braided element, polypropylene, stainless steel, nitinol, silicone, polyethylene, polytetrafluoroethylene, resorbable synthetic polymers, polylactide, polyglycolide, polydioxanone, polycaprolactone, and co-polymers thereof.

10. A system for treating obstructive sleep apnea comprising:
- an anchoring element adapted to be embedded in soft tissue of an inframandibular region to form a soft anchor of scar tissue therein;
- a tongue implant implantable in a tongue, said tongue implant having a buttress and at least one arm extending from said buttress; and
- said at least one arm of said tongue implant being attachable to said anchoring element for coupling said tongue implant with said anchoring element, wherein spacing between said buttress of said tongue implant and said anchoring element is adjustable by pulling said at least one arm through said anchoring element, wherein said at least one arm comprises a first arm extending from a first end of said buttress, said first arm having a first set of barbs projecting therefrom, and a second arm extending from a second end of said buttress, said second arm having a second set of barbs projecting therefrom.

11. The system as claimed in claim 10, wherein said barbs projecting from said first and second arms are adapted to engage said anchoring element for coupling said tongue implant and said anchoring element together.

12. The system as claimed in claim 11, wherein the spacing between said central buttress section of said tongue implant and said anchoring element is adjustable by pulling said first and second arms through said anchoring element, and wherein said barbs collapse inwardly when said arms are pulled in a first direction and flex outwardly for engaging said anchoring element when said arms are pulled in a second, opposite direction for resisting movement in the second direction.

13. The system as claimed in claim 10, wherein said tongue implant comprises materials selected from the group consisting of monofilaments, barbed monofilaments, braided elements, barbed braided elements, sutures and barbed sutures, and said anchoring element comprises materials selected from the group consisting of biocompatible mesh, biocompatible fabric, woven mesh, knitted mesh, non-woven mesh, non-knitted mesh, a braided element, polypropylene, stainless steel, nitinol, silicone, polyethylene, polytetrafluoroethylene, resorbable synthetic polymers, polylactide, polyglycolide, polydioxanone, polycaprolactone, and co-polymers thereof.

14. A method of treating obstructive sleep apnea comprising:
- forming scar tissue in an inframandibular region to create a soft anchor, wherein the forming scar tissue comprises implanting a flexible layer in the inframandibular region and forming said scar tissue at least partially around said flexible layer;
- implanting a tongue implant in a tongue, said tongue implant having at least one arm extending therefrom;
- advancing said at least one arm through said tongue and toward the inframandibular region for coupling said tongue implant with said scar tissue;
- pulling said at least one arm through said flexible layer for adjusting spacing between said tongue implant and said flexible layer.

15. The method as claimed in claim 14, further comprising providing a sclerosing agent on said flexible layer.

16. The method as claimed in claim 14, wherein said flexible layer comprises a mesh or fabric.

17. The method as claimed in claim 14, wherein said at least one arm is coupled with said scar tissue using sutures, clips, barbs, knots, or adhesive.

18. The method as claimed in claim 14, wherein pulling said at least one arm through said flexible layer shifts said tongue anteriorly.

19. A system for treating obstructive sleep apnea comprising:
- an anchoring element adapted to be embedded in soft tissue of an inframandibular region to form a soft anchor of scar tissue therein;
- a tongue implant implantable in a tongue, said tongue implant having a buttress and at least one arm extending from said buttress; and
- said at least one arm of said tongue implant being attachable to said anchoring element for coupling said tongue implant with said anchoring element;
- wherein said at least one arm comprises: a first arm extending from a first end of said buttress, said first arm having a first set of barbs projecting therefrom, and a second arm extending from a second end of said buttress, said second arm having a second set of barbs projecting therefrom;
- wherein said barbs projecting from said first and second arms are adapted to engage said anchoring element for coupling said tongue implant and said anchoring element together;
- wherein spacing between said central buttress of said tongue implant and said anchoring element is adjustable by pulling said first and second arms through said anchoring element.

* * * * *